(12) United States Patent
Finocchiaro et al.

(10) Patent No.: US 8,613,971 B2
(45) Date of Patent: Dec. 24, 2013

(54) USE OF EXTRUDED STARCH-BASED COMPLEXES FOR SATIETY, REDUCTION OF FOOD INTAKE, AND WEIGHT MANAGEMENT

(75) Inventors: Eugene Terry Finocchiaro, West Amwell, NJ (US); Matthew R. Park, Milltown, NJ (US); Tushar Shah, Jersey City, NJ (US)

(73) Assignee: Corn Products Development, Inc., Westchester, IL (US)

( * ) Notice: Subject to any disclaimer, the term of this patent is extended or adjusted under 35 U.S.C. 154(b) by 0 days.

(21) Appl. No.: 13/077,320

(22) Filed: Mar. 31, 2011

(65) Prior Publication Data

US 2012/0251659 A1    Oct. 4, 2012

(51) Int. Cl.
*A23L 1/0522*  (2006.01)
*A23L 1/0526*  (2006.01)

(52) U.S. Cl.
USPC .......................................... 426/658; 426/661

(58) Field of Classification Search
USPC ................................................ 426/658, 661
See application file for complete search history.

(56) References Cited

U.S. PATENT DOCUMENTS

| | | | |
|---|---|---|---|
| 5,755,890 A * | 5/1998 | Yuan | 127/71 |
| 7,235,276 B2 | 6/2007 | Allen et al. | |
| 2005/0208180 A1 | 9/2005 | Engleson et al. | |
| 2006/0078593 A1 | 4/2006 | Strozier et al. | |
| 2006/0188642 A1 | 8/2006 | Yakubu et al. | |
| 2006/0210695 A1 | 9/2006 | Ganjyal et al. | |
| 2006/0292287 A1 | 12/2006 | Onwulata | |
| 2008/0233260 A1 * | 9/2008 | Woo et al. | 426/575 |

FOREIGN PATENT DOCUMENTS

| | | |
|---|---|---|
| WO | 2005092115 A1 | 10/2005 |
| WO | 2006130713 A1 | 12/2006 |
| WO | 2007094943 A1 | 4/2007 |

OTHER PUBLICATIONS

Onwulata, C., I. Konstance, R. P., Cooke, P. H. and Farrell, Jr. H.M. "Functionality of Extrusion—Texturized Whey Proteins" J. Dairy Sci. 86: 3775-3782.

* cited by examiner

*Primary Examiner* — Jyoti Chawla
(74) *Attorney, Agent, or Firm* — Thomas C. McKenzie; Karen Kaiser

(57) ABSTRACT

The present invention relates to starch-hydrocolloid complexes, their preparation and their use in foods. The complexes positively impact the foods into which they are incorporated to give longer-lasting and/or more potent satiety, thereby helping energy management. The invention further relates to the reduction of food intake and/or management of weight by increasing such satiety.

8 Claims, 6 Drawing Sheets

FIG 1A

Stomach/Intestinal Viscosity Sample Preparation Experimental Design

Figure 1C:
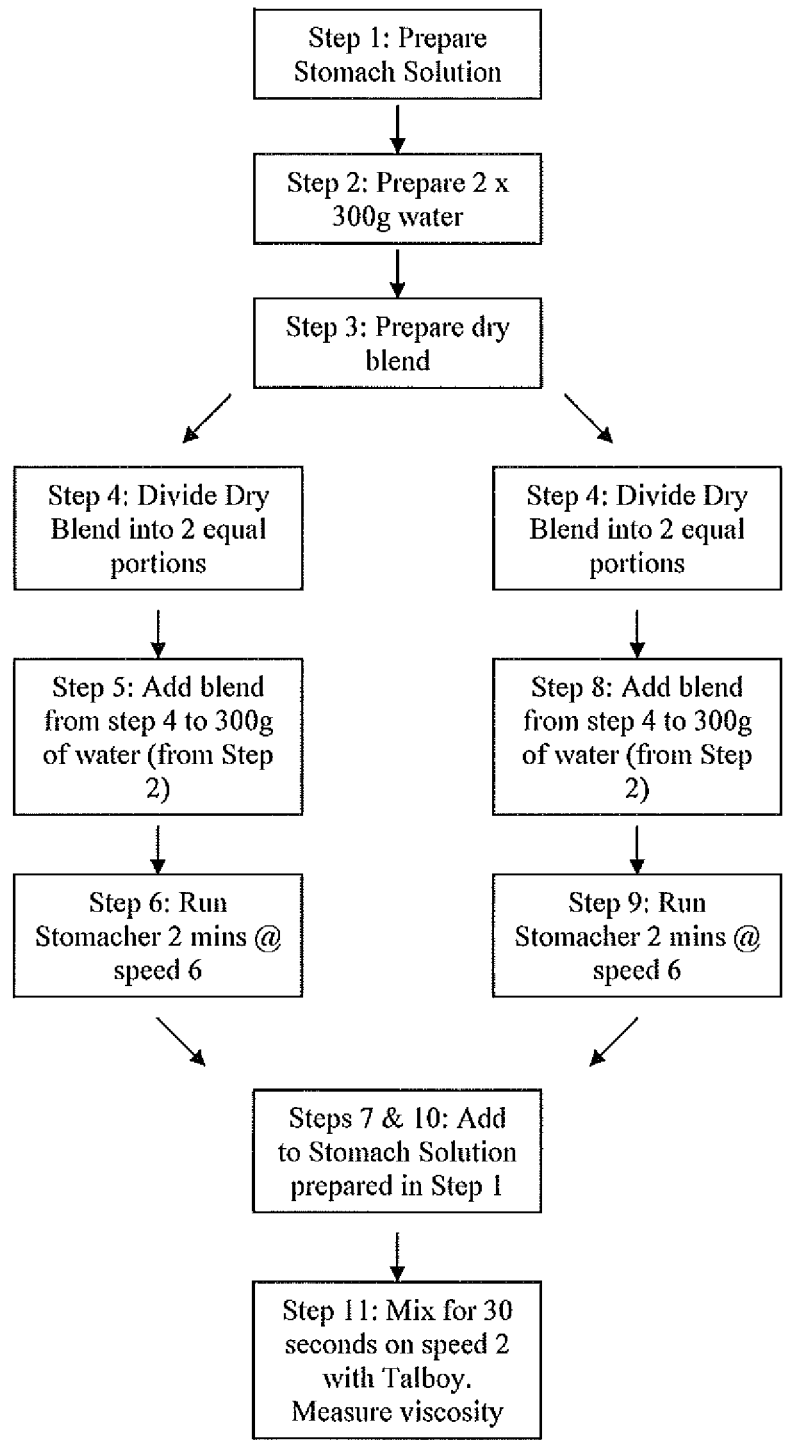

Method (Neat Form):
1. Measure out stomach model ingredients (standardized to 1.25 liters) into stomach vessel and place in waterbath (37.5 °C)
   i. Water, DI     277.5 ml
   ii. 0.2M potassium hydrogen phthalate (40.844g potassium hydrogen phthalate in 1 liter water     207.5 ml
   iii. 1.0M NaOH (Sigma 930-65)     18.8 ml
   iv. Gastric mucosa mucin solution (1.5g gastric mucosa mucin in 50 ml water)     43.1 ml
   v. 0.2% pepsin solution (0.20g pepsin in 100 ml water)     43.1 ml
2. Heat 2 sets of 300g of DI water to 37 °C in waterbath
3. Weigh out required amount of Composite (see table below)
4. Divide the blended material into 2 equal portions
5. Add the 300g of pre-heated water from step 2 and half the active blend weighed out in step 4 to stomacher bag
6. Run stomacher for 120 seconds at speed 6 (with paddles set at 15.8mm)
7. Add contents of stomacher bag to stomach model solution prepared in step 1
8. Add the 2nd 300g of pre-heated water from step 2 and the other half of the blend to the same stomacher bag
9. Run stomacher for 120 seconds at speed 6 (with paddles set at 15.8mm)
10. Add contents of stomacher bag to the same stomach model solution prepared in step 1 (already containing ingredients from step 7)
11. Mix sample for 30 seconds using the Talboy stirrer on speed 2. The stirrer should be position in the middle of the vessel, with the mixing paddle 15cm below the rim of the vessel (lined up with mark on stirrer shaft). All sediment should be stirred up.
12. Measure sample viscosity (see below for test method)

Composite (no blending with Maltodextrin)

| Composite Composition | Dose Level (g/liter stomach) | Dose Level (g/1.25 liter stomach) | Notes |
|---|---|---|---|
| 80:20 Starch:Hydrocolloid | 30 | 37.5 | Level standardized to 6g/liter stomach of hydrocolloid |
| 70:30 Starch:Hydrocolloid | 20 | 25 | Level standardized to 6g/liter stomach of hydrocolloid |

FIG 1B

Viscosity Settings:
- Unit: Brookfield RVDV-II+Pro with temperature probe
- Mixing: Mix all samples with Talboy unit for 30 seconds on speed 2 before measuring viscosity
- Spindle Set: RV
- Spindle #: 2 or 3
- Speed: 50
- # Data Points: 120*
    *collect 125; disregard first 5

Figure 2 – Screw Configuration
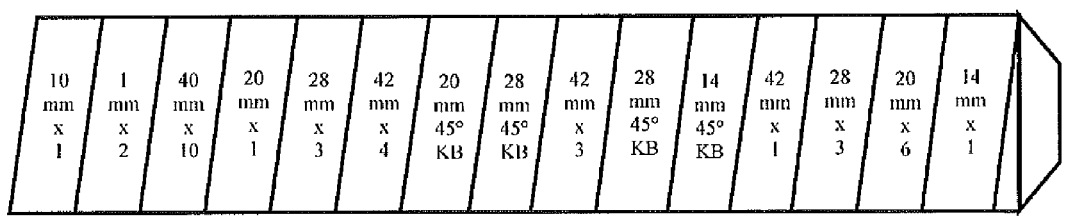
KB = Kneading Block

Figure 3 – Heating Zone Diagram (Starch-Guar Complexes)

| 13 | 12 | 11 | 10 | 9 | 8 | Feed ＼／ 7 | H₂0 ＼／ 6 | 5 | 4 | 3 | 2 | 1 | Die Plate |
|----|----|----|----|---|---|---|---|---|---|---|---|---|---|
|    |    |    |    |   |   | Zone 2 / Temp. 2 | | Zone 3 / Temp. 3 | | Zone 4 / Temp. 4 | | Zone 5 / Temp. 5 | |

Figure 4 – Heating Zone Diagram (Starch-Guar-Oil Complexes)

| 13 | 12 | 11 | 10 | 9 | 8 | Feed \ / 7 | H₂O \ / 6 | 5 | Oil \ / 4 | 3 | 2 | 1 | Die Plate |
|---|---|---|---|---|---|---|---|---|---|---|---|---|---|
| | | | | | | Zone 2 / Temp. 2 | | Zone 3 / Temp. 3 | | Zone 4 / Temp. 4 | | Zone 5 / Temp. 5 | |

US 8,613,971 B2

USE OF EXTRUDED STARCH-BASED COMPLEXES FOR SATIETY, REDUCTION OF FOOD INTAKE, AND WEIGHT MANAGEMENT

FIELD OF THE INVENTION

The present invention relates to starch-hydrocolloid complexes, their preparation and their use in foods.

SUMMARY OF THE INVENTION

The present invention relates to starch-hydrocolloid complexes, their preparation and their use in foods. The complexes positively impact the foods into which they are incorporated to give longer-lasting and/or more potent satiety, preferably without any adverse affect on the processing or texture of specified food products, which may help energy management. The invention further relates to the reduction of food intake and/or management of weight by increasing such satiety.

The present invention addresses the major limitations associated with existing state-of art ingredients for satiety: robust clinical efficacy in a form that is edible and process compatible in food products. The unique combination of resistant starch and hydrocolloid enables a more potent or more robust satiety effect by combining two physiological satiety mechanisms. Further, the unique complexation of these two components enables higher resistant starch (RS) content and improved texture by controlling the hydration of the hydrocolloid, particularly in a food product, without adversely affecting clinical efficacy. Typically, when high levels of commercially available resistant starch and hydrocolloid are incorporated into foods, processability and eating quality suffers. This invention allows for higher levels of resistant starch while minimizing the deleterious effects of such starch and/or hydrocolloids in foods, thus enabling superior eating quality and textural benefits vs. a comparable "dry blend" control which may have higher water-binding and gumminess from the uncomplexed hydrocolloid.

The term "complex" is meant to include two or more ingredients that have been co-processed to form a material in which the ingredients are not physically separable.

The term "dry blend" is meant to include two or more ingredients combined to form a material in which the ingredients are physically separable.

The term "hydrocolloid" is meant to include any viscosifying gum with a neutral charge (non-ionic).

The term "resistant starch (RS)" is defined as the sum of starch and starch degradation products that are not absorbed in the small intestine of healthy individuals and is measured by treatment with pancreatic alpha-amylase and amyloglucosidase (AMG) using a modification of the Englyst method, described in the Examples section. It is inclusive of all resistant starch known in the art. Resistant starch product is intended to mean a product containing resistant starch.

"High resistant starch content" is intended to mean a resistant starch content of at least 70% by weight based on the weight of the starch.

The term "high amylose" is used herein, is defined as containing at least 27% amylase for wheat or rice and at least about 50% amylose for other sources, particularly at least about 70%, more particularly at least about 80% amylose by weight based of the starch. The percent amylose is determined by using the potentiometric test described in the Examples section.

The term "increased satiety", as used herein, is intended to mean that the caloric intake at least within the two hours after consumption of the complex is reduced by at least 10% compared to consumption of a readily digestible 10 DE (dextrose equivalent) maltodextrin of equal caloric content (e.g., STAR-DRI 100, commercially available from Tate & Lyle, Decatur, Ill., USA).

The term "oil" as used herein, is intended to mean any oil, fat or triglyceride from any source.

Mammal, as used herein, is intended to include humans.

DETAILED DESCRIPTION OF FIGURES

FIG. 1: Stomach/Intestinal Viscosity Sample Preparation Experimental Design—Set forth as FIGS. 1A, 1B and 1C FIG. 2: Screw Configuration used in example 1

FIG. 3: Heating Zone Diagram (Starch-Guar Complexes) used to process the Complexes in Example 1.

FIG. 4: Heating Zone Diagram (Starch-Guar-Oil Complexes) used to process the Complexes in Table 14.

DETAILED DESCRIPTION OF THE INVENTION

The present invention relates to starch-hydrocolloid complexes, their preparation and their use in foods to increase satiety in mammals. Optionally these complexes may contain oil as a third ingredient. The invention also relates to the reduction of caloric intake as a consequence of inducing satiety, which may aid in weight management.

The starch component of the complex (hereinafter inclusive of starch containing materials such as flours, grits and whole grains) is a resistant starch product and may be derived from any native source which is high in amylose. A native starch as used herein, is one as it is found in nature. Also suitable are starches derived from a plant obtained by standard breeding techniques including crossbreeding, translocation, inversion, transformation or any other method of gene or chromosome engineering to include variations thereof. In addition, starch derived from a plant grown from induced mutations and variations of the above generic composition which may be produced by known standard methods of mutation breeding are also suitable herein.

Typical sources for the starch are cereals, tubers, roots, legumes and fruits. The native source include without limitation high amylose varieties of corn (maize), pea, potato, sweet potato, banana, barley, wheat, rice, sago, amaranth, tapioca, arrowroot, canna, or sorghum. In one embodiment, the starch is a high amylose corn starch.

In another embodiment, the plant source is one having an amylose extender genotype, the component starch comprising less than 10% by weight amylopectin. This grain is derived from a plant breeding population, particularly corn, which is a genetic composite of germplasm selections and its starch comprises at least 75% by weight amylose, optionally at least 85% amylose (i.e., normal amylose) as measured by butanol fractionation/exclusion chromatography techniques. The starch further comprises less than 10%, by weight, optionally less than 5%, amylopectin and additionally from about 8 to 25% low molecular weight amylose. The grain is preferably derived from a plant having a recessive amylose extender genotype coupled with numerous amylose extender modifier genes. This grain and its method of preparation are described in U.S. Pat. No. 5,300,145, the specification of which is incorporated herein by reference.

The resistant starch product of the complex may be derived directly from a native source, and/or may be physically, chemically or enzymatically modified. In one embodiment, the resistant starch product is a high amylose product sourced from corn. In a further embodiment, the resistant starch product is a granular resistant starch, also known as a type-2 resistant starch. In yet another embodiment, the resistant starch product is a high amylose, granular corn starch. In still yet another embodiment, the resistant starch product is prepared by hydrothermal treatment as described for example in U.S. Pat. Nos. 5,593,503 and 5,902,410 and US Publication Nos. 2002-0197373 and 2006-0263503, the specifications of which are incorporated herein by reference. In one embodiment, the predominant granular structure of the starch is not completely destroyed though it may be partially swollen as long as its crystallinity is not completely destroyed. Accordingly, the term "granular starch" as used herein, means a starch which retains at least part of its granular structure thereby exhibiting some crystallinity, so that the granules are birefringent and the Maltese cross is evident under polarized light.

The combination of moisture-temperature-time for hydrothermal treatment may vary dependent upon the type of starch used. In general, the total water (moisture) content will be in a range of from about 10 to 50%, and in one embodiment in the range of from about 20 to 30% by weight based on the weight of the dry starch. The starch is heated at a target temperature of from about 60 to 160° C., and in one embodiment at a temperature of from about 100 to 120° C. The time of heating at the target temperature may vary depending on the starch used, its amylose content and particle size, the level of total dietary fiber content desired as well as the amount of moisture and the heating temperature. In one embodiment, such heating time will be from about 1 minute to 24 hours, and in one embodiment from 1 to 3 hours.

In one embodiment of the invention, the starch has a resistant starch content of at least 70%, in another embodiment at least 75%, and in yet another embodiment at least 80% by weight of the starch.

The hydrocolloid component of the complex may be any viscosifying gum with a neutral charge (non-ionic) and is intended to include without limitation guar gum, konjac, locust bean gum, tam gum, and other such exocellular polysaccharides. In one embodiment, the hydrocolloid component is guar gum. In yet another embodiment, the gum is a high viscosity gum with a viscosity specification between 4,000-5,500 cps (1% aqueous solution @ 25° C. using a Brookfield RVT, spindle #4 @ 20 RPM).

The complex has a ratio (wt/wt) of starch:hydrocolloid of at least 70:30. In one embodiment, the ratio (wt/wt) of starch:hydrocolloid is at least 80:20. In yet another embodiment, the complex has a ratio (wt/wt) of starch:hydrocolloid of no more than 95:5.

In one embodiment, the starch is a high amylose corn resistant starch and the hydrocolloid is a guar gum. In yet another embodiment, the starch is a hydrothermally treated high amylose corn resistant starch and the hydrocolloid is a guar gum.

The complex may optionally include at least one oil. Throughout this specification the terms oil and fat are used interchangeably. The terms are meant to include triglycerides from either vegetable and/or animal sources. Such vegetable triglycerides include soybean oil, sunflower oil, palm oil, palm kernel oil, both high and low erucic rapeseed oil, coconut oil, olive oil, sesame oil, peanut oil, corn oil and mixtures thereof. Triglycerides from animal sources include fish oil, tallow, sardine oil, dairy fat and mixtures thereof. In one embodiment, the oil is selected from the group consisting of canola oil and sunflower oil.

The oils may be chemically, physically and/or genetically modified products such as hydrogenated, fractionated and/or inter-esterified triglyceride mixtures and mixtures of two or more thereof, as well as edible substances that are physically similar to triglycerides such as waxes, e.g. jojoba oil, and poly fatty acid esters mono- or disaccharides, that may be used as replacement for or in a mixture with triglycerides.

When used, the oil is present in an amount of from 10% to 25% by weight of the complex.

In one aspect of the invention, the complex contains no caloric components other than the starch and the hydrocolloid components and in another aspect no caloric components other than the starch, the hydrocolloid and the oil.

The complex may be prepared by any physical process which allows the mixture of the starch and hydrocolloid to be combined under heat and/or pressure so as to no longer be capable of being physically separated. In one aspect of the invention, the complex is prepared by extrusion using heat and/or pressure.

The extrusion apparatus may be any screw-type extruder known in the art and in one embodiment is a twin-screw extruder. In one aspect of the invention, the temperature is controlled along at least part of the length of the extruder. In another aspect, the components are extruded at temperatures between 80° C.-100° C. In yet another aspect, the components are extruded at temperatures between 85° C.-95° C.

In one aspect of the invention, the starch and hydrocolloid are mixed in a ribbon blender or a V-blender to form a dry blend. Water, either alone or as part of an aqueous solution or dispersion is then added to hydrate the dry blend in the extruder to form a complex. If oil is to be added, it is added after hydration. In one embodiment, the oil is added downstream of the water, yet far enough upstream to uniformly incorporate it into the starch-hydrocolloid mixture to form a complex.

After the starch and hydrocolloid complex is prepared, it may be further processed. Such further processing includes without limitation, methods known in the art such as drying, grinding, agglomeration with or without additional ingredients, and pH adjustment.

Drying includes any method known in the art, including without limitation spray drying, flash drying, air drying, freeze drying, vacuum drying, belt drying, and drum drying. In one embodiment, the pH of the complex is adjusted to between 5.5 and 8.0.

The resultant complex has high resistant starch content. In one embodiment of the invention, the complex has a resistant starch content of at least 70% by weight of the starch. In another embodiment, the complex has a resistant starch content of at least 75% by weight of the starch. In yet another embodiment, the complex has a resistant starch content of at least 80% by weight of the starch. This resistant starch content is measured using the method set forth in the Example section.

The resultant complex has high viscosifying ability and has been quantified in an in vitro stomach viscosity assay. In one embodiment of the invention, the complex has an in vitro stomach viscosity content of at least 75% of area under the curve (AUC) vs. guar gum. In another embodiment of the invention, the complex has an in vitro stomach viscosity content of at least 80% of AUC vs. guar gum. In yet another embodiment of the invention, the complex has an in vitro stomach viscosity content of at least 85% of AUC vs. guar gum. In still yet another embodiment of the invention, the complex has an in vitro stomach viscosity content of at least 90% of AUC vs. guar gum. This in vitro stomach viscosity content is measured using the method set forth in the Example section.

In one aspect of the invention, the resultant complex may have a delayed lipolysis profile of at least 57% vs. heavy cream. In another aspect, the complex has a delayed lipolysis profile of at least 62% vs. heavy cream. In yet another aspect, the complex may have a delayed lipolysis profile of at least 8% vs. Slimthru (commercially available from DSM, England) and containing Fabuless, an emulsion of palm and oat oils). In a further aspect, the complex may have a delayed lipolysis profile of at least 19% vs. Slimthru.

The complex is fed to a mammal. In one embodiment, the mammal is a companion animal, including without limitation, dogs and cats. In another embodiment, the mammal is a human.

The complex is effective such that consumption is effective to increase satiety by reducing caloric intake at least within the two hours following consumption by at least 10% compared to consumption of a readily digestible 10 DE (dextrose equivalent) maltodextrin of equal calorie content. In another embodiment, the complex is effective in an amount of at least 7.5 grams, in another embodiment at least 10 grams, in yet another embodiment at least 15 grams, and in still yet another embodiment at least 20 grams. In one aspect, the caloric intake is reduced by at least 15% using any of the above criteria. In a further aspect, the caloric intake is reduced by at least 20% using any of the above criteria. In another aspect, the caloric increase is reduced within the 24 hour period following consumption using the same criteria. Such decreased caloric intake may further result in increased weight loss.

The resultant complex of this invention may be eaten as is or incorporated into a variety of foods that include, but are not limited to, cold form snack bars, baked goods such as muffins and cookies, ready-to-eat cereals, pasta and other low-moisture food systems. Food products are also intended to include nutritional products, including but not limited to, prebiotic and synbiotic compositions, diabetic foods and supplements, dietetic foods, foods to control glycemic response and tablets and other pharmaceutical dosage forms. Food products comprise the complex and at least one additional edible ingredient.

When added to a food product, the resultant complex is added in any amount desired. In one aspect, the complex is added in an amount of from 5 to 75% (w/w) of the food product and in another aspect in an amount of from 10 to 65% (w/w) of the food product. In one embodiment, the complex is added in an amount of at least 10% (w/w) based upon the food. In another embodiment, the complex is added in an amount of at least 15% (w/w) based upon the food. In yet another embodiment, the complex is added in an amount of at least 20% (w/w) based upon the food. In still yet another embodiment, the complex is added in an amount of at least 25% (w/w) based upon the food. In a further embodiment, the complex is added in an amount of at least 30% (w/w) based upon the food. In yet a further embodiment, the complex is added in an amount of at least 35% (w/w) based upon the food. In still yet a further embodiment of the invention, the complex is substituted for at least part of the flour or other carbohydrate-based product conventionally added to the food, for example, by replacing the conventional starch, flour, grit or grain.

Addition of the starch-hydrocolloid complex to foods may not significantly affect the organoleptic quality attributes of the food in any deleterious way, including texture (gumminess) or flavor, and may, in some cases, provide favorable organoleptic changes. The addition of the complex to foods may increase the nutritional value of the food, such as the resistant starch and/or dietary fiber content.

EXAMPLES AND METHODOLOGIES

The following examples are presented to further illustrate and explain the present invention and should not be taken as limiting in any regard. All parts, ratios, and percentages are given by weight and all temperatures in degrees Celsius (° C.) unless otherwise noted.

The following ingredients were used throughout the examples.

HYLON® VII high amylose (contains at least 70% amylose) corn starch containing approximately 80% resistant starch and 16% TDF, commercially available from National Starch LLC.

Hi-maize® 260 hydrothermally treated high amylose starch commercially available from National Starch LLC.

Coyote Brand™ Guar Gum HV consisting chiefly of high molecular weight galactomannan commercially available from Gum Technology Corporation.

Centrabest Canola oil, commercially available from Bunge Oils.

The following test procedures were used throughout the examples:

A. Resistant Starch ("RS") Determination (Modified Englyst Method)

Resistant starch content was determined using a modified version of the Englyst Digestion Method (Englyst et. al., European Journal of Clinical Nutrition, vol. 46 (Suppl. 2), pp S33-S50, 1992). The procedure and modifications are detailed below. Rapidly digestible starch (RDS) is defined as the amount of glucose released at 20 minutes; slowly digestible starch (SDS) is defined as the amount of glucose released between 20 minutes and 120 minutes; resistant starch (RS) is the starch not hydrolyzed after 120 minutes of incubation. RS content is determined indirectly by measuring the amount of digested carbohydrate (i.e., free glucose) after 120 min. of incubation, then calculating RS by subtracting the amount of free glucose from carbohydrate to give % RS based on the carbohydrate content.

In vitro glucose release results were adjusted to take into account only the total starch portion of the material and not the total carbohydrate content. The hydrocolloid, lipid and protein amounts were subtracted out of the sample weight assayed based on their percentage in the complex. This was done to determine the RS content based on the total starch portion of the complex. Including the weight of the non-starch materials would result in artificially higher complex RS content.

Preparation of Standard Solutions, Enzyme Solutions, Blanks and Glucose Controls:
 a. Reaction "blank" consisted of 20 ml of 0.25M sodium acetate.
 b. Glucose standard consisted of 20 ml 0.25M sodium acetate buffer plus 500 mg glucose.
 c. Stock solution A was prepared by dissolving 0.5% (w/v) pepsin (porcine stomach mucosa (P7000) from Sigma) plus 0.5% (w/v) guar gum (G-4129 guar gum from Sigma) in 0.05M HCl.
 d. Preparation of purified enzyme solution: 12 g of porcine pancreatin (Sigma) was dissolved in 85 mls of de-ionized room temperature water. The solution was subsequently centrifuged (3000 rpm, 10 min, 50 ml tubes) and the supernatant was decanted off and saved.

e. Stock solution B was prepared by adding 40 mg of dry invertase (Sigma) and 1.0 ml amyloglucosidase (AMG) (300L AMG from Novozymes) to the aforementioned supernatant.

Determination of RS Content (Modified Englyst Protocol):

Each test sample was weighed (to the nearest 0.1 mg) to deliver 550-600 mg of carbohydrate in each test tube. 10 mls of Solution A was then added to each tube. Samples were covered tightly, mixed, and then incubated in a quiescent water bath @ 37° C. for 30 minutes. Ten mls of 0.25M sodium acetate buffer was added to neutralize the solution. Next, 5 mls of enzyme mixture (solution B) was added to the samples, blank, and glucose tubes @ 20-30 second intervals, and placed into the 37° C. water bath for digestion. Tubes were shaken horizontally during digestion. At 120 minutes of digestion time, 0.5 ml aliquots were removed and placed into separate tubes of 19 mls of 66% ethanol to stop the reaction (enzyme will precipitate; re-disperse before next step). 1.0 ml aliquot of the ethanolic solution was then pipetted into 1 ml micro-centrifuge tubes and centrifuged for 5 min. @ 3000 g. Glucose concentrations were subsequently measured using the glucose oxidase/peroxidase (GOPOD) method (Megazyme Kit K-Glue). Three ml of GOPOD was placed into each culture tube and 0.1 ml of each sample was added, mixed well and incubated for 20 minutes at 50° C. Free glucose was determined spectrophotometrically for absorbance at 510 nm wavelength. The percent glucose (digestion) for each sample is calculated based on the UV absorbance relative to the standards. Routine controls were run that included a reference sample of regular dent corn. All analyses were run at least in duplicates.

B. Moisture Content ("% M") Determination:

The moisture content of extruded complexes was determined using a Sartorius electronic moisture analyzer (model MA 30) available from Sartorius AG. Moisture balance was set to 105° C. on "Auto" mode. In this mode, MA 30 recognizes when a considerable weight change is no longer expected (when moisture loss per unit of time reaches zero, or the readout remains constant for a short time after a slight decrease in weight) and automatically ends the moisture determination routine.

C. Amylose Content by Potentiometric Titration:

0.5 g of a starch (1.0 g of a ground grain) sample was heated in 10 mls of concentrated calcium chloride (about 30% by weight) to 95° C. for 30 minutes. The sample was cooled to room temperature, diluted with 5 mls of a 2.5% uranyl acetate solution, mixed well, and centrifuged for 5 minutes at 2000 rpm. The sample was then filtered to give a clear solution. The starch concentration was determined polarimetrically using a 1 cm polarimetric cell. An aliquot of the sample (normally 5 mls) was then directly titrated with a standardized 0.01N iodine solution while recording potential using a platinum electrode with a KCl reference electrode. The amount of iodine needed to reach the inflection point was measured directly as bound iodine. The amount of amylose was calculated by assuming 1.0 gram of amylose will bind with 200 milligrams of iodine.

D. Measurement of Guar Gum Viscosity:

The Brookfield viscosity of guar is determined using the procedure listed below (Cold Brookfield Viscosity Analysis Method: B-V-1.03B, Polypro International, Inc.). A sample is dispersed in water and allowed to hydrate; the Brookfield viscosity is read at specified times.

Apparatus:
1. Waring blender, consumer model (minimum 360 Watt motor)
2. Quart blender cup (stainless or glass)
3. Variac, 0-140 volts
4. Balance, accurate +/−0.01 grams
5. Graduated cylinder, 500 ml
6. Beaker, Griffin Low Form, 600 ml
7. Stopwatch
8. Brookfield RV viscometer with spindles
9. Constant temperature water bath
10. Stirring rod
11. Weigh boat
12. Thermometer Chemicals and Reagents:
Distilled or deionized water (pH adjusted to 5.5-6.0)

Procedure:
A. Preparation of water
1. Adjust pH to 5.5-6.0 (use dilute Nitrogen Gas or HCl)
2. Adjust temperature to 25° C.
B, Calibration
1. Assure that the Brookfield pointer moves freely and is properly calibrated according to the manufacturer's instructions
2. Set pH meter to read 7.00+/−0.01 with 7.00 buffer
C. Analytical Procedure
1. Weigh 5.00+/−0.01 grams of gum to be tested into a weigh boat
2. Measure 495+/−2 ml of distilled or deionized water into a Waring blender cup set on a blender base
3. Adjust the speed of the blender so as to form a vortex half way between the blender blade and top of the water (approximately 1500-1800 rpm)
4. Guar lumps will not go into solution and contribute to inaccurate viscosity readings. Avoid letting the powder come into contact with the walls of the blender cup or hub of mixing blade. To form a lump free solution, direct the gum to the top of the slope of the vortex. Simultaneously start the stopwatch and rapidly dump the guar into the agitating water.
5. Continue mixing for 2 minutes. As the solution thickens, slightly increase the blade speed to maintain a slight vortex. Keep air entrapment to a minimum. At 2 minutes, transfer solution into a 600 ml Griffin Low Form beaker. Void test if lumps are visible.
6. Maintain the solution temperature at 25° C. in the constant temperature water bath
7. Use 20 rpm viscometer speed. Normally, the #3 spindle will be used. The #2 spindle may be required if the viscosity is initially lower than 1300 cps.
8. Viscosity readings will be taken at 15 minutes, 30 minutes, 1 hour, 2 hours, 4 hours and 24 hours after mix. At 1 minute before the required reading, remove the beaker containing the solution from the bath, stir the solution with a glass rod, place under the viscometer and install the spindle. At 20 seconds before the reading, turn on the viscometer, read at the specified time.
9. At 2 hours read and record pH. Some time may be required to reach a stable reading due to viscous nature of the solution.

E. Measurement of Stomach/Intestinal Viscosity:

A bench-top stomach model was developed and includes features derived from other stomach models referenced in the literature (Kimura et al., 2000, National Enzyme Co./TNO Nutrition and Food Research, 2004). This digestive model also simulates the buffering capacity of stomach components in the "fed" state, as distinguished from other stomach models run in a "fasted" or empty-stomach state. In order to standardize the digestion process and to improve the reproducibility of the procedure in the laboratory, some simplifying assumptions were made:

Size of the stomach, 1.25 liters.
Simulation of mastication by stomacher pre-treatment, no salivary amylase used.
Agitation: By reciprocating shaker platform, 120 rpm, constant throughout run.
Temperature: 37° C. fixed throughout (vessels immersed in temperature-regulated water bath); normal human body temperature.
Stomach media components:
   Pepsin (from porcine gastric mucosa—e.g., Sigma P7000); activated from pepsinogen by low pH conditions, breaks down protein components to peptides and is most active between pH 2-4.
   Mucin (protective protein; e.g. Type II, Sigma M2378); since pepsin comes from the cells of the stomach walls, it was decided to include the mucin protective proteins in the systems which also derives from the stomach walls.
   pH 5.0 buffer system: potassium hydrogen phthalate (e.g., Sigma 179922)/NaOH (e.g. 1.0N solution, Sigma S2567). Simulates the presence of some food, not as strong a buffer as acetate.
Stomach stage: 2 hours with HCl addition. Rate of acid HCl addition in stomach stage assumed to be 36 milliequivalents (mEq) per hour at a constant rate (0.50 ml/min of 1.5N HCl for 1.25 liter stomach volume). Acid added drop-wise onto the liquid surface through a metered peristaltic pump. pH shifted from ~5.0-~2.0 in 2 hours stomach stage.
Neutralization: Performed by the addition of 15 ml 6N NaOH (solution from pellets, e.g., Sigma S8045) and 15 g NaHCO$_3$ (e.g., Sigma S6014): By using a combination of NaOH and NaHCO$_3$, the pH shift may be accomplished quickly without excess foaming (as in the case of NaHCO$_3$ alone) and without driving the pH too high above the target pH of 7.0 (as in the case of NaOH alone).
Intestine stage 2 hours: Enzyme present in intestine: pancreatin (porcine source, e.g., Sigma P8096), a blend of amylase, lipase, protease and ribonuclease. Not included in this simulation are bile acids (also called bile salts).
Note also that glucose release (GR), as well as resistant starch levels are measured in a separate analytical test (Englyst et al., 1992).

F. Determination of Proteolysis/Lipolysis:

A simple bench-top method was developed and validated to measure and simulate the rate of digestion of fat and protein as they pass through a human digestive system. The purpose of this method was to provide comparative in vitro data on the relative rates of fat digestion of food samples in simulated human digestive media. The method was validated using commercial ingredients exhibiting both rapid (heavy cream) and slow (Slimthru®) lipid/protein digestion.

The method yielding the best differentiation between the products tested consists of a process which begins by simulating an empty stomach wherein the sample in solution with pepsin begins digestion at a pH of 5.5; the pH is then adjusted down to 2.0 in increments of 0.5 at 15 minute intervals over a 2 hour incubation period. The pH of the solution is titrated back to the set pH using 0.2N HCl at the end of each 15 minute interval, prior to adjustment down to the next pH. The volume of HCl added to the solution throughout the digestion is recorded as a measure of the rate of protein digestion. At the end of 2 hours of stomach simulation, small intestine digestion is simulated by adjusting the pH to 7.5 and adding pancreatin and bile salts. The pH is checked at 15 minute intervals over the next 2 hours and readjusted as necessary to 7.5 using 0.1N NaOH. The volume of NaOH added to the digestion solution to maintain pH 7.5 is recorded as a measure of the rate of fat digestion.

Proteolysis is considered to have occurred when the protein in the samples has been sufficiently hydrolyzed to create a shift in pH that may be titrated with dilute hydrochloric acid. The proteolysis rate is proportional to the amount of hydrochloric acid solution necessary to return to the initial pH over that measured period of time.

Lipolysis is considered to have occurred when sufficient quantities of free fatty acids have been liberated from triglyceride molecules in the digestion media to allow titration by a measurable quantity of dilute sodium hydroxide solution. The lipolysis rate is proportional to the amount of sodium hydroxide solution necessary to maintain a constant pH over a measured period of time.

Example 1

Extruded Starch-Guar Complexes

A representative extrusion was conducted under the following conditions. Hi-maize® 260 starch was pre-blended with guar gum at prescribed ratios in Table 1 in a Patterson-Kelley (PK) Liquid/Solids V-blender (model 0204920) for 5 minutes.

The composition of each extruded starch-guar dry blend is set forth in Table 1 below.

TABLE 1

Extruded Starch-Guar Complex Ingredients and Dry Blend Formulations

| Notebook No. | Ingredient | Level (%) | Lot |
|---|---|---|---|
| 527:1-12P | Hi-maize ® 260 starch | 80.00 | BHI 0088 |
| | Coyote Brand ™ Guar Gum HV | 20.00 | 07F5A001Z |
| 527:1-13P | Hi-maize ® 260 starch | 70.00 | BHI 0088 |
| | Coyote Brand ™ Guar Gum HV | 30.00 | 07F5A001Z |

A K-Tron loss-in-weight feeder was used to feed the resulting dry blend into the extruder. Starch-guar extruded complexes were prepared using a Werner Pfleiderer twin screw extruder (model ZSK-30) with a length to diameter (L/D) ratio of 21 with a screw configuration having a combination of conveying screws and four kneading blocks. 7 barrels were used, screw diameter was 30 mm, and the die opening was 5 mm (×2).

The screw configuration used is listed as FIG. 2 in the drawings.

Heating Zone Diagram 1 was used to process the complexes as seen in FIG. 3 in the drawings.

The feed rate was kept constant at 10 kg/hr, Water was added to the extruder just after the feed at a rate of 2.9 to 4.3 kg/hr. The screws were operated at a speed of 250 rpm and the barrel temperature profiles were set at 60° C. for zone 3, 90° C. for zone 4, and 110° C. for zone 5. During extrusion, the extruder zones were heated using oil to achieve set points for barrel temperatures.

The starch-guar extrusion conditions are set forth in Table 2 below.

TABLE 2

Extruded Starch-Guar Gum Complex Processing Conditions

| Notebook No. | Calculated Barrel Moisture (%) | Screw Speed (RPM) | Barrel Temp. Profile (° C.) Zone 1/2/3/4 | Torque (%) | Product Temp. (° C.) | Pressure (kPa) | SME (Wh/kg) |
|---|---|---|---|---|---|---|---|
| 527:1-12 | 30.8 | 250 | 24/52/78/101 | 38 | 99 | 552 (gauge) 653 (absolute) | 139 |
| 527:1-13 | 33.0 | 250 | 24/53/79/100 | 38 | 97 | 690 (gauge) 791 (absolute) | 133 |

During extrusion, the pressure at the die ranged from 552-690 kPa (gauge) or 653-791 kPa (absolute), torque readings were approximately 38%, product temperatures ranged from 97° C. to 99° C., and Specific Mechanical Energy (SME) values were calculated to be between 133-139 Wh/kg.

A die cutter was not used; extruded ropes were broken up by hand and oven-dried at 75° C. overnight to achieve a final moisture content between 3% and 8% by weight. Extrudates were ground using a Mikro-Bantam™ Mill (model CF) using screen 250 (0.25 inch or 0.60 cm size openings). Ground material was screened through a US #10 mesh sieve. Material through a US #10 mesh sieve was used for in vitro and applications screening.

In Vitro Glucose Release (GR) Using a Modified Englyst Assay

Table 3 shows RS content increased by≈31% and 23% for 80:20 and 70:30 Hi-maize® 260 starch:guar gum extruded complexes, respectively versus comparable dry blends. 80:20 and 70:30 Hi-maize® 260 starch:guar gum extruded complexes exhibited≈38% and 43% increased RS compared to native Hi-maize® 260 starch.

TABLE 3

In vitro Glucose Release Results for Hi-maize ® 260 starch-Guar Gum Extruded Complexes

| Ingredient Complex | Notebook No. | Moisture (%) | In vitro GR (%)[1] 20 min. | 120 min. | 240 min. | RDS (% db) | SDS (% db) | RS (% db) |
|---|---|---|---|---|---|---|---|---|
| Hm 260 starch (Native) | NA | 10.0 | 35 | 52 | 59 | 35 | 17 | 48 |
| Hm 260 starch (Extruded) | 527:1-11 | 2.6 | 47 | 60 | 59 | 47 | 13 | 40 |
| 80:20 Hm 260 starch: Guar gum | 527:1-12P Dry blend | 11.4 | 10 | 46 | 49 | 10 | 36 | 54 |
| | 527:1-12 Complex | 3.1 | 11 | 22 | 29 | 11 | 11 | 78 |
| 70:30 Hm 260 starch: Guar gum | 527:1-13P Dry blend | 10.9 | 10 | 35 | 34 | 10 | 25 | 65 |
| | 527:1-13 Complex | 3.2 | 8 | 16 | 20 | 8 | 8 | 84 |

[1]Based on total starch content

Although RS content is an important performance criteria, gastrointestinal (GI) viscosifying ability and organoleptics are also important. For those determinations, test complexes and various controls were formulated into cold processed bars, and then tested for in vitro GI viscosity and for sensory attributes.

Bar Formulations and Preparations

A cold form snack bar formulated with test ingredients and controls was used to evaluate textural attributes and measure in vitro stomach viscosity. The wet (ingredient) phase, consisting of corn syrup (63 DE), fig paste (23% moisture) and orange flavor (added post-heating), was prepared by heating to 60° C. (140° F.) to soften and aid blend uniformity. The heated wet phase was then added to the pre-blended dry phase consisting of rolled oats, granulated sugar, rice flour and salt. The blended mass was then portioned into 40 g pieces and transferred into bar molds. The bars were formulated to deliver a soft texture, with a moisture content of ≈18% and a water activity of less than 0.60. Further refinement work was carried out on the snack bar formulation to develop a control for stomach model and sensory evaluations. A Control bar was formulated to match the nutritional profile, solids content and texture/firmness of the bars with complexes, and was evaluated as a reference point. To achieve this, the rice flour was decreased and the sugar and rolled oats levels increased to bring up the solids content and balance the carbohydrate level (target 80% carbohydrate). Whey protein (Instantized BiPRO® from Davisco Foods International, Inc.) was added at 0.09% to balance the protein level (target 5% protein) and canola oil was added at 1.10% to balance the fat level (target 2.5% fat).

Bar formulations are shown in Table 4 below.

TABLE 4

Bar Formulations Used for Evaluation of Extruded Starch-Guar Complexes

| Ingredient | Control | Control + 70:30 Complex | Control + 80:20 Complex |
|---|---|---|---|
| Dries | | | |
| Extruded Complex | — | 16.670 | 23.080 |
| Rolled Oats, Chopped | 21.600 | 17.348 | 16.014 |
| Sugar, EFG | 9.090 | 8.627 | 7.964 |
| Rice Flour (White) | 14.175 | — | — |
| Whey Protein (BiPRO ®) | 0.090 | — | — |
| Salt | 0.045 | 0.047 | 0.043 |
| Total | 45.000 | 42.693 | 47.101 |
| Wets | | | |
| Fig Paste (23%M) | 27.528 | 28.682 | 26.476 |
| Corn Syrup (DE 63) | 26.043 | 28.281 | 26.106 |
| Canola oil | 1.100 | — | — |
| Nat. Orange Flv. WONF | 0.330 | 0.344 | 0.317 |
| Total | 55.001 | 57.307 | 52.899 |

Sensory Evaluation, Bars with Test Ingredients:

Sensory evaluation of snack bars was conducted by a sensory panel consisting of the same five individuals. Baseline sensory scores were established for the control bar. Extruded complexes and dry blend controls were evaluated in the control bar base. The serving size of the bars was adjusted to accommodate for the different compositions of the materials, standardizing the total amount of control bar base used to 33.3 g per serving. This resulted in a serving size of 43.3 g for the 80:20 complexes (4.6% gum level by total formulation) and 40.0 g for the 70:30 complexes (5.0% gum level by total formulation). This adjustment was made to keep the same amount of control bar base being added into the Stomach/Intestine Viscosity Model for each complex run.

Four attributes, hardness, chewiness, gumminess and off-flavor were rated on a 9-point hedonic scale. For gumminess and off-flavor, a score of 4 was classified as borderline acceptable and 5 or above as unacceptable. Chewiness and hardness were ranked based on personal perception of bars, for example a granola bar being a 9 and a fruit bar being a 1. Snack bar samples were made on the bench top the day before evaluation (stored in a sealed container at room temperature) to allow the bars to equilibrate. Sensory scores were averaged across the five panelists to allow comparisons to be made. The key attributes identified as primary modes of failure were gumminess and off-flavor.

Sensory results in Table 5 demonstrate bars made with starch-guar gum complexes scored lower with regard to gumminess vs. bars made with the unprocessed dry blends.

TABLE 5

Sensory Testing Results for Bars Made with Starch-Guar Complexes vs. Dry Blend Controls

| | | 80:20 Hi-maize ® 260 starch:Guar Gum | | 70:30 Hi-maize ® 260 starch:Guar Gum | |
|---|---|---|---|---|---|
| Attribute | Control | Complex 527:1-12 | Dry blend 527:1-12P | Complex 527:1-13 | Dry blend 527:1-13P |
| Hardness | 3.2 | 5.0 | 5.2 | 4.0 | 4.2 |
| Chewiness | 4.8 | 5.0 | 3.8 | 5.7 | 4.0 |
| Gumminess | 2.3 | 2.5 | 6.7 | 2.8 | 5.0 |
| Off-flavor | 1.2 | 2.3 | 2.5 | 1.5 | 2.1 |

In Vitro Stomach/Intestinal Viscosity

Bars containing test ingredients were run through the stomach model assay as detailed above. All samples, including the fully hydrated guar gum gold standard reference, were assayed at equivalent guar gum levels. Intestinal phase viscosity data is presented as % area under the curve (AUC) vs. the fully hydrated guar gum reference. The data in Table 6 shows the gum from the complex displays over 76% of viscosifying power when compared to the fully hydrated gum reference. Guar gum is fully hydrated using a standard process known in the art.

TABLE 6

Extruded Complex Stomach Viscosity Model % of Gold Standard Intestinal Area under the Curve in Bar Application

| Ingredient Complex | % of Gold Standard with Bar Solids (Intestine AUC) |
|---|---|
| Guar Gum Gold Standard[1] | 100 |
| 80:20 Hi-maize ® 260 starch:Guar gum | 88 |
| 70:30 Hi-maize ® 260 starch:Guar gum | 76 |

[1]Gold Standard is 6 g/L guar gum pre-hydrated and added to bar solids (7.5 grams of pre-hydrated guar gum + 125 grams of bar base per 1.25 L)

Example 2

Extruded Starch-Guar Complexes

A representative extrusion was conducted under the following conditions. Hi-maize® 260 starch was pre-blended with guar gum at prescribed ratios in Table 7 in a Bepex Corporation ribbon blender (model IMS-1).

The composition of the extruded starch-guar dry blend is set forth in Table 7 below.

TABLE 7

Extruded Starch-Guar Complex Ingredients and Dry Blend Formulation

| Notebook No. | Ingredient | Level (%) | Lot |
|---|---|---|---|
| 527:19-2P | Hi-maize ® 260 starch | 80.00 | EJI 2233 |
| | Coyote Brand ™ Guar Gum HV | 20.00 | 08H4A001Z |

A K-Tron loss-in-weight feeder was used to feed the resulting dry blend into the extruder. Starch-guar extruded complex was prepared using a Buhler twin screw extruder (model 44D) with a length to diameter (L/D) ratio of 28 with a screw configuration having a combination of conveying screws and two small 15 mm reverse elements. 6 barrels were used, screw diameter was 44 mm, and the die opening was 7 mm (×2).

The screw configuration used is listed below:
1(sd5) 2(66) 1(15)r 2(66) 1(44) 1(66) 2(44) 1(66) 2(44) 1(33) 1(44) 1(33) 1(44) 2(33) 1(44) 1(33) 1(44) 2(33) 1(44) 1(15)r 3(33) 1(44)

The feed rate was kept constant at 30 kg/hr. Water was added to the extruder just after the feed at a rate of 10.0 kg/hr. The screws were operated at a speed of 200 rpm and barrel temperature profiles were set at 30° C. for zone 1, 30° C. for zone 2, 50° C. for zone 3, and 50° C. for zone 4. Two Mokon heating units containing oil were used to keep barrel temperatures constant. A die cutter with four flex blades was utilized to allow for more efficient drying in the fluidized bed drier.

The starch-guar extrusion conditions are set forth in Table 8 below.

TABLE 8

Extruded Starch-Guar Gum Complex Processing Conditions

| Notebook No. | Calculated Barrel Moisture (%) | Screw Speed (RPM) | Barrel Temp. Profile (° C.) Zone 1/2/3/4 | Torque (%) | Product Temp. (° C.) | Pressure (kPa) | SME (Wh/kg) |
|---|---|---|---|---|---|---|---|
| 527:19-2 | 33.3 | 200 | 31/30/49/49 | 38 | 95 | 2,100 (gauge) 2,201 (absolute) | 83 |

During extrusion, the pressure at the die was 2,100 kPa (gauge) or 2,201 kPa (absolute), torque reading was approximately 38%, product temperature was 95° C., and Specific Mechanical Energy (SME) was calculated to be 83 Wh/kg.

The extrudates were collected in a basket off the extruder and placed into a Buhler fluidized bed drier set at 45° C. The basket was left in the fluidized bed drier until the extrudate moisture content was below 10% by weight. Dried extrudates were ground using a Mikro-Bantam™ Mill (model CF) using screen 250 (0.25 inch or 0.60 cm size openings). Ground material was screened through a US #40 mesh sieve. Material through a US #40 mesh sieve was used for in vitro and applications screening.

In vitro Glucose Release (GR) Using a Modified Englyst Assay

Table 9 shows RS content increased by≈23% for Hi-maize® 260 starch:guar gum extruded complex versus a dry blend. Hi-maize® 260 starch:guar gum extruded complex exhibited ≈38% increased RS compared to native Hi-maize® 260 starch.

Although RS content is an important performance criteria, gastrointestinal (GI) viscosifying ability and organoleptics are also important. For those determinations, test complexes and various controls were formulated into cold processed bars, and then tested for in vitro GI viscosity and for sensory attributes.

Bar Formulations and Preparations

A cold form snack bar formulated with test ingredients and controls was used to evaluate textural attributes and measure in vitro stomach viscosity. The wet (ingredient) phase, consisting of corn syrup (63 DE), fig paste (23% moisture) and orange flavor (added post-heating), was prepared by heating to 60° C. (140° F.) to soften and aid blend uniformity. The heated wet phase was then added to the pre-blended dry phase consisting of rolled oats, granulated sugar, rice flour and salt. The blended mass was then portioned into 40 g pieces and transferred into bar molds. The bars were formulated to deliver a soft texture, with a moisture content of≈18% and a water activity of less than 0.60. Further refinement work was carried out on the snack bar formulation to develop a control for stomach model and sensory evaluations. A Control bar was formulated to match the nutritional profile, solids content and texture/firmness of the bars with complexes, and was evaluated as a reference point. To achieve this, the rice flour was decreased and the sugar and rolled oats levels increased to bring up the solids content and balance the carbohydrate level (target 80% carbohydrate). Whey protein (Instantized BiPRO® from Davisco Foods International, Inc.) was added at 0.09% to balance the protein level (target 5% protein) and canola oil was added at 1.10% to balance the fat level (target 2.5% fat).

TABLE 9

In vitro Glucose Release Results for Hi-maize ® 260 starch-Guar Gum Extruded Complexes

| Ingredient Complex | Notebook No. | Moisture (%) | In vitro GR (%)[1] | | | RDS (% db) | SDS (% db) | RS (% db) |
|---|---|---|---|---|---|---|---|---|
| | | | 20 min. | 120 min. | 240 min. | | | |
| Hm 260 starch (Native) | NA | 10.0 | 35 | 52 | 59 | 35 | 17 | 48 |
| Hm 260 starch: Guar gum | 527:19-2P Dry blend | 10.8 | 16 | 41 | 47 | 16 | 25 | 59 |
| | 527:19-2 Complex | 12.7 | 7 | 23 | 24 | 7 | 17 | 77 |

[1] Based on total starch content

Bar formulations are shown in Table 10 below.

TABLE 10

Bar Formulations Used for Evaluation of Extruded Starch-Guar Complexes

| Ingredient | Control | Control + 80:20 Complex |
|---|---|---|
| Dries | | |
| Extruded Complex | — | 23.080 |
| Rolled Oats, Chopped | 21.600 | 16.014 |
| Sugar, EFG | 9.090 | 7.964 |
| Rice Flour (White) | 14.175 | — |
| Whey Protein (BiPRO ®) | 0.090 | — |
| Salt | 0.045 | 0.043 |
| Total | 45.000 | 47.101 |
| Wets | | |
| Fig Paste (23%M) | 27.528 | 26.476 |
| Corn Syrup (DE 63) | 26.043 | 26.106 |
| Canola oil | 1.100 | — |
| Nat. Orange Flv. WONF | 0.330 | 0.317 |
| Total | 55.001 | 52.899 |

Sensory Evaluation, Bars with Test Ingredients:

Sensory evaluation of snack bars was conducted as in example 1. Baseline sensory scores were established for the control bar. Extruded complexes and dry blend controls were evaluated in the control bar base. The serving size of the bars was adjusted to accommodate for the different compositions of the materials, standardizing the total amount of control bar base used to 33.3 g per serving. This resulted in a serving size of 43.3 g for the 80:20 complex (4.6% gum level by total formulation). This adjustment was made to keep the same amount of control bar base being added into the Stomach/Intestine Viscosity Model for each complex run.

Four attributes, hardness, chewiness, gumminess and off-flavor were rated on a 9-point hedonic scale. For gumminess and off-flavor, a score of 4 was classified as borderline acceptable and 5 or above as unacceptable. Chewiness and hardness were ranked based on personal perception of bars, for example a granola bar being a 9 and a fruit bar being a 1. Snack bar samples were made on the bench top the day before evaluation (stored in a sealed container at room temperature) to allow the bars to equilibrate. Sensory scores were averaged across the five panelists to allow comparisons to be made. The key attributes identified as primary modes of failure were gumminess and off-flavor.

Sensory results in Table 11 demonstrate bars made with the extruded starch-guar gum complex scored lower with regard to gumminess and off-flavor vs. bars made with the unprocessed dry blend.

TABLE 11

Sensory Testing Results for Bars Made with Starch-Guar Complexes vs. Dry Blend Controls

| | | 80:20 Hi-maize ® 260 starch:Guar Gum | |
|---|---|---|---|
| Attribute | Control | Complex 527:19-2 | Dry blend 527:19-2P |
| Hardness | 3.2 | 5.0 | 3.1 |
| Chewiness | 4.8 | 3.6 | 4.4 |
| Gumminess | 2.3 | 2.4 | 5.6 |
| Off-flavor | 1.2 | 1.8 | 3.0 |

In Vitro Stomach/Intestinal Viscosity

Bars containing test ingredients were run through the stomach model assay as detailed above. All samples, including the fully hydrated guar gum gold standard reference, were assayed at equivalent guar gum levels. Intestinal phase viscosity data is presented as % area under the curve (AUC) vs. the fully hydrated guar gum reference. The data in Table 12 shows the gum from the complex displays 91% of viscosifying power when compared to the fully hydrated gum reference. Guar gum is fully hydrated using a standard process known in the art.

TABLE 12

Extruded Complex Stomach Viscosity Model % of Gold Standard Intestinal Area under the Curve in Bar Application

| Ingredient Complex | % of Gold Standard with Bar Solids (Intestine AUC) |
|---|---|
| Guar Gum Gold Standard[1] | 100 |
| 80:20 Hi-maize ® 260 starch:Guar gum 527:19-2 | 91 |

[1]Gold Standard is 6 g/L guar gum pre-hydrated and added to bar solids (7.5 grams of pre-hydrated guar gum + 125 grams of bar base per 1.25 L)

Example 3

Extruded Starch-Guar-Oil Complexes

A representative extrusion was conducted under the following conditions. High amylose corn-based resistant starches (HYLON® VII starch or Hi-maize® 260 starch) were pre-blended with guar gum at the prescribed ratios in Table 13 in a Patterson-Kelley (PK) Liquid/Solids V-blender (model 0204920) for 5 minutes. Starch-guar gum dry blend ratios were based on delivering 3 g of guar and 3 g of canola oil per 20 g dose, and 5 g of guar and 4 g of canola oil per 20 g dose.

TABLE 13

Starch-Guar-Oil Extruded Complex Dry Blend Formulations

| Notebook No. | Ingredient | Level (%) | Lot |
|---|---|---|---|
| 527:9-3P | HYLON ® VII starch | 81.250 | BH 9830 |
| | Coyote Brand ™ Guar Gum HV | 18.750 | 07F5A001Z |
| 527:9-4P | HYLON ® VII starch | 66.672 | BH 9830 |
| | Coyote Brand ™ Guar Gum HV | 33.328 | 07K5A007Z |
| 527:9-5P | Hi-maize ® 260 starch | 81.250 | HH 5976 |
| | Coyote Brand ™ Guar Gum HV | 18.750 | 07K5A007Z |
| 527:9-6P | Hi-maize ® 260 starch | 66.672 | HH 5976 |
| | Coyote Brand ™ Guar Gum HV | 33.328 | 07K5A007Z |

A K-Tron loss-in-weight feeder was used to feed the resulting dry blend into the extruder. Starch-Guar-Oil extruded complexes were prepared using a Werner Pfleiderer model ZSK-30 twin screw extruder with a length to diameter (L/D) ratio of 21 with a screw configuration having a combination of conveying screws and four kneading blocks.

Screw configuration used is listed as FIG. 2 in the drawings.

Heating Zone Diagram 1—FIG. 4 in the drawings was used to process the complexes. Canola oil (Bunge Oils CENTRA-BEST Canola oil Lot F609L) was metered into barrel 4 using a pump to achieve target oil levels of 15% and 20% in the finished complex. 7 barrels were used, screw diameter was 30 mm, die opening was 5 mm (×2).

Feed rate was kept constant at 10 kg/hr. Water was added to the extruder just after the feed at a rate of 3.5 to 4.0 kg/hr. The screws were operated at a speed of 250 rpm and the barrel heating zones were set to 0° C. for zone 1, 0° C. for zone 2, 60° C. for zone 3, 90° C. for zone 4, 110° C. for zone 5. During extrusion, the extruder zones were heated using oil to achieve set points for barrel temperatures.

The starch-guar-oil extrusion conditions are set forth in Table 14 below.

TABLE 14

Extruded Starch-Guar-Oil Complex Processing Conditions

| Notebook No. | Calculated Barrel Moisture (%) | Screw Speed (RPM) | Barrel Temp. Profile (° C.) 1/2/3/4/5 | Torque (%) | Product Temp. (° C.) | Pressure (kPa) | SME (Wh/kg) |
|---|---|---|---|---|---|---|---|
| 527:9-3 | 34.7 | 250 | NA/23/50/75/98 | 27.5 | 84 | 138 (gauge) 239 (absolute) | 85 |
| 527:9-4 | 35.0 | 250 | NA/21/49/75/98 | 28.0 | 82 | 0 | 82 |
| 527:9-5 | 33.8 | 250 | NA/22/52/76/99 | 27.5 | 85 | 0 | 85 |
| 527:9-6 | 34.3 | 250 | NA/23/52/76/98 | 25.0 | 81 | 0 | 74 |

During extrusion, the pressure at the die ranged from 0-138 kPa (gauge) or 0-239 kPa (absolute), torque readings were in the range of 25% to 28%, product temperatures ranged from 81° C. to 85° C., and SME values were calculated to be between 74 Wh/kg-85 Wh/kg. A die cutter was not used; extruded ropes were broken up by hand and oven-dried at 65° C. overnight to achieve a final moisture between 7% and 10% by weight. Extrudates were ground using a Mikro-Bantam™ Mill (model CF) using screen 250 (0.25 inch or 0.60 cm size openings). Ground material was screened through a US #10 mesh sieve. Material through a US #10 mesh sieve was used for in vitro and applications screening.

In vitro GR results shown in Table 15 demonstrate extruded complexes containing higher levels of guar gum and canola oil exhibited increased RS and showed delayed in vitro GR profiles for each starch base. RS content and in vitro GR profiles were similar for both Hylon® VII starch and Hi-maize® 260 starch complexes containing comparable amounts of guar gum and canola oil.

TABLE 15

In vitro Glucose Release Results for Starch-Guar-Oil Extruded Complexes

| Ingredient Complex | Notebook No. | Extrudate Moisture (%) | In vitro GR (%)[1] | | | RDS (% db) | SDS (% db) | RS (% db) |
|---|---|---|---|---|---|---|---|---|
| | | | 20 min. | 120 min. | 240 min. | | | |
| 68.3% HYLON VII starch: 15.8% Guar: 15.9% Canola | 527:9-3 | 9.2 | 22 | 35 | 40 | 22 | 13 | 65 |
| 53.4% HYLON VII starch: 26.7% Guar: 19.9% Carola | 527:9-4 | 8.4 | 5 | 18 | 23 | 5 | 13 | 82 |
| 68.2% Hi-maize 260 starch: 15.7% Guar: 16.1% Canola | 527:9-5 | 7.2 | 19 | 30 | 36 | 19 | 11 | 70 |
| 52.5% Hi-maize 260 starch: 26.2% Guar: 21.3% Canola | 527:9-6 | 8.4 | 9 | 21 | 32 | 9 | 12 | 79 |

[1]Based on total starch content

Lipolysis Profiles:

Neat test ingredients were testing in the in vitro lipolysis assay (referenced above) and compared to a commercial benchmark (Slimthru®) and a normally digested lipid (heavy pasteurized cream). Table 16 shows relative lipolysis rates for HYLON® VII and Hi-maize® 260 extruded complexes versus Slimthru® and heavy cream. Complex 527:9-6 exhibited the slowest lipolysis rate, 62% vs. heavy cream and 19% compared to Slimthru®. Complex 527:9-3 showed a delayed lipolysis rate of 60% vs. heavy cream and 15% compared to Slimthru®. Complex 527:9-5 exhibited a slower lipolysis rate of 57% vs. heavy cream and 9% vs, Slimthru®.

TABLE 16

Relative Lipolysis Rates for Extruded Starch-Guar-Oil Complexes versus Slimthru ® Benchmark and Heavy Cream

| Ingredient | Relative Lipolysis Rate vs. Heavy Cream |
|---|---|
| Heavy Cream | 1.00 |
| Slimthru ® (Contains DSM Fabuless ™) | 0.47 |
| 53% Hi-maize 260 starch/26% Guar/ 21% Canola 527:9-6 | 0.38 |
| 68% HYLON VII starch/16% Guar/16% Canola 527:9-3 | 0.40 |
| 68% Hi-maize 260 starch/16% Guar/ 16% Canola 527:9-5 | 0.43 |
| 53% HYLON VII starch/27% Guar/20% Canola 527:9-4 | 0.53 |

Bar Formulations and Preparations:

A cold formed snack bar similar to example 1 was used to evaluate extruded starch-guar-oil complexes. Table 17 shows bar formulations used to evaluate extruded complex textural attributes.

Due to difficulty in uniformly incorporating canola oil into the starch-guar dry blend, canola oil was added separately for evaluation of the bars prepared with dry blends. For the dry blend bars, bar base was split into required bar base weights in separate KitchenAid® bowls. Canola oil was added to each dry blend bar based on the oil content of the complex. Bar base was blended at speed 1 for 1 minute. Dry blend was mixed in at speed 1 for 1 minute (mixed further for an additional minute if necessary).

TABLE 17

Complex Bar Formulations Used for Evaluation of Extruded Starch-Guar-Oil Complexes

| Ingredient | Control | 527:9-3 | 527:9-4 | 527:9-5 | 527:9-6 |
|---|---|---|---|---|---|
| Dries | | | | | |
| Extruded Complex | 0.00 | 27.56 | 18.35 | 27.60 | 18.60 |
| Complex Dry blend | 0.00 | 23.18 | 14.7 | 23.16 | 14.65 |
| Canola oil | | 4.38 | 3.65 | 4.44 | 3.95 |
| Rolled Oats, Chopped | 20.82 | 15.08 | 17.00 | 15.07 | 16.95 |
| Sugar, EFG | 10.35 | 7.50 | 8.45 | 7.50 | 8.43 |
| Salt | 0.06 | 0.04 | 0.05 | 0.04 | 0.04 |
| Total | 31.23 | 50.18 | 43.85 | 50.21 | 44.02 |
| Wets | | | | | |
| Fig Paste (23%M) | 34.42 | 24.93 | 28.10 | 24.92 | 28.02 |
| Corn Syrup (DE 63) | 33.94 | 24.58 | 27.71 | 24.57 | 27.63 |
| Nat. Orange Flv. WONF | 0.41 | 0.31 | 0.34 | 0.30 | 0.33 |
| Total | 68.77 | 49.82 | 56.15 | 49.79 | 55.98 |

Sensory Evaluation, Bars with Test Ingredients:

Sensory evaluation of snack bars was conducted as in example 1. Baseline sensory scores were established for the control bar. Extruded complexes and dry blend controls were evaluated in the control bar base. The serving size of the bars was adjusted to accommodate for the different guar gum compositions of the materials, standardizing the total amount of control bar base used to 33.3 g per serving. This resulted in a serving size of 46.0 g for the lower guar gum (≈15.8%)/canola oil (≈16.0%) level complexes (5.0% guar gum level by total formulation) and 40.9 g for the higher guar gum (≈26.5%)/canola oil (≈20.6%) level complexes (5.0% gum level by total formulation). This adjustment was made to keep the same amount of control bar base being added into the Stomach/Intestine Viscosity Model for each complex run. Appropriate amount of canola oil was added on top of the bar with the starch-guar dry blend to simulate complex with oil.

Four attributes, hardness, chewiness, gumminess and off-flavor were rated on a 9-point hedonic scale. For gumminess and off-flavor, a score of 4 was classified as borderline acceptable and 5 or above as unacceptable. Chewiness and hardness were ranked based on personal perception of bars, for example a granola bar being a 9 and a fruit bar being a 1. Snack bar samples were made on the bench top the day before evaluation (stored in a sealed container at room temperature) to allow the bars to equilibrate. Sensory scores were averaged across the five panelists to allow comparisons to be made. The key attributes identified as primary modes of failure were gumminess and off-flavor.

Sensory results in Tables 18 and 19 demonstrate bars made with starch-guar-oil complexes scored lower with regard to gumminess and off-flavor versus bars made with dry blend controls.

TABLE 18

Sensory Testing Results for Bars Made with HYLON ® VII-Guar Gum-Canola Oil Extruded Complexes vs. Dry Blend Controls

| | | 68.3% HYLON ® VII starch/15.8% Guar/ 15.9% Canola Oil | | 53.4% HYLON ® VII starch/26.7% Guar/ 19.9% Canola Oil | |
|---|---|---|---|---|---|
| Attribute | Control | Complex 527:9-3 | Dry blend 527:9-3P | Complex 527:9-4 | Dry blend 527:9-4P |
| Hardness | 3.2 | 6.7 | 5.2 | 4.4 | 4.2 |
| Chewiness | 4.8 | 3.6 | 4.6 | 4.4 | 4.6 |
| Gumminess | 2.3 | 2.5 | 5.8 | 3.5 | 4.6 |
| Off-flavor | 1.2 | 1.9 | 2.1 | 1.7 | 2.4 |

TABLE 19

Sensory Testing Results for Bars Made with Hi-maize ® 260 starch-Guar Gum-Canola Oil Extruded Complexes vs. Dry Blend Controls

| | | 68.2% Hi-maize ® 260 starch/15.7% Guar/ 16.1% Canola Oil | | 52.5% Hi-maize ® 260 starch/26.2% Guar/ 21.3% Canola Oil | |
|---|---|---|---|---|---|
| Attribute | Control | Complex 527:9-5 | Dry blend 527:9-5P | Complex 527:9-6 | Dry blend 527:9-6P |
| Hardness | 3.2 | 7.4 | 5.1 | 4.7 | 4.5 |
| Chewiness | 4.8 | 4.2 | 3.9 | 4.4 | 4.2 |
| Gumminess | 2.3 | 2.4 | 6.0 | 3.2 | 5.0 |
| Off-flavor | 1.2 | 1.6 | 2.3 | 1.6 | 1.4 |

In Vitro Stomach/Intestinal Viscosity

Bars containing test ingredients were run through the stomach viscosity model assay as detailed above. All samples, including the fully hydrated guar gum gold standard reference, were assayed at equivalent guar gum levels. Intestinal phase viscosity data is presented as % area under the curve (AUC) vs. the fully hydrated guar gum reference. The data in Table 20 shows the gum from the complex displays over 77% of viscosifying power when compared to the fully hydrated gum reference, very similar to complexes prepared without oil.

TABLE 20

Extruded Complex Stomach Viscosity Model % of Gold Standard Intestinal Area under the Curve in Bar Application

| Ingredient Complex | % of Gold Standard with Bar Solids (Intestine AUC) |
|---|---|
| Guar Gum Gold Standard[1] | 100 |
| 68.3% HYLON ® VII starch 15.8% Guar gum 15.9% Canola oil | 89 |
| 53.4% HYLON ® VII starch 26.7% Guar gum 19.9% Canola oil | 85 |
| 68.2% Hi-maize ® 260 starch 15.7% Guar gum 16.1% Canola oil | 84 |
| 52.5% Hi-maize ® 260 starch 26.2% Guar gum 21.3% Canola oil | 77 |

[1]Gold Standard is 6 g/L guar gum pre-hydrated and added to bar solids (7.5 grams of pre-hydrated guar gum + 125 grams of bar base per 1.25 L)

What is claimed is:

1. A complex comprising a starch which contains a starch with a resistant starch content of at least 70% (w/w) and a hydrocolloid; wherein the starch is a hydrothermally treated starch and the complex is prepared by extrusion using heat and/or pressure; wherein the starch is a high amylose corn starch; and wherein the hydrocolloid is guar gum; and wherein the starch and hydrocolloid complex has a ratio (w/w) of starch:hydrocolloid of at least 70:30.

2. The complex of claim 1, further comprising an oil.

3. The complex of claim 2, wherein the oil is present in an amount of from 10-25% (w/w) based on the complex.

4. A food product comprising the complex of claim 1 and an additional edible ingredient.

5. The food product of claim 4, wherein the complex is in an amount of from 5 to 75% (w/w).

6. The complex of claim 1, wherein the starch is a granular resistant starch, also known as a type-2 resistant starch.

7. The complex of claim 1, wherein the complex has a ratio (w/w) of starch:hydrocolloid of at least 80:20.

8. The complex of claim 1, wherein the complex is extruded at temperatures between 85° C.-95° C.

* * * * *